(12) United States Patent
Kawaguchi et al.

(10) Patent No.: US 11,498,032 B2
(45) Date of Patent: Nov. 15, 2022

(54) CONCENTRATION APPARATUS

(71) Applicant: Murata Manufacturing Co., Ltd., Nagaokakyo (JP)

(72) Inventors: Toshikazu Kawaguchi, Nagaokakyo (JP); Junko Watanabe, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 16 days.

(21) Appl. No.: 16/726,291

(22) Filed: Dec. 24, 2019

(65) Prior Publication Data

US 2020/0129925 A1 Apr. 30, 2020

Related U.S. Application Data

(63) Continuation of application No. PCT/JP2018/022886, filed on Jun. 15, 2018.

(30) Foreign Application Priority Data

Jul. 3, 2017 (JP) .............................. JP2017-130613

(51) Int. Cl.
*B01D 61/18* (2006.01)
*B01D 61/22* (2006.01)
(Continued)

(52) U.S. Cl.
CPC .............. *B01D 61/18* (2013.01); *B01D 61/22* (2013.01); *B01D 71/022* (2013.01);
(Continued)

(58) Field of Classification Search
CPC ........ C12M 1/12; C12M 29/18; C12M 33/14; C12M 47/02; C12M 47/10; C12N 9/00;
(Continued)

(56) References Cited

U.S. PATENT DOCUMENTS

| 4,722,902 A | 2/1988 | Harm et al. |
| 4,952,127 A * | 8/1990 | Schmeisser ............ C12M 47/02 494/1 |

(Continued)

FOREIGN PATENT DOCUMENTS

| JP | S62171669 A | 7/1987 |
| JP | H0267452 A | 3/1990 |

(Continued)

OTHER PUBLICATIONS

Rennels et al., Pipe Flow: A Practical and Comprehensive Guide, AIChE, John Wiley & Sons, ISBN 978-0-470-90102-1 (Year: 2012).*

(Continued)

*Primary Examiner* — Allison G Fitzsimmons
(74) *Attorney, Agent, or Firm* — ArentFox Schiff LLP

(57) ABSTRACT

A concentration apparatus that includes a liquid tank storing a liquid containing a filtration object, a tubular member having first and second end portions disposed in the liquid tank and forming a first circulation flow path therebetween, a circulation pump for supplying the liquid stored in the liquid tank to flow from the first end portion to the second end portion, a filtration filter disposed in a sidewall of the tubular member, a bypass pipe having first and second ends thereof connected to sidewalls of the tubular member so as to form a second circulation flow path between the first and second end portions of the tubular member, a switching valve constructed to cause the liquid to flow in one of the first or second circulation flow paths, and a control unit controlling driving of the circulation pump and a switching operation of the switching valve.

15 Claims, 10 Drawing Sheets

(51) Int. Cl.
*B01D 71/02* (2006.01)
*B01D 71/00* (2006.01)

(52) U.S. Cl.
CPC .... *B01D 2313/083* (2013.01); *B01D 2313/18* (2013.01); *B01D 2313/243* (2013.01)

(58) Field of Classification Search
CPC ......... C12P 13/001; C12P 13/04; C12P 13/08; C12P 19/34; C12P 1/00; C12P 21/02; C12P 7/02; C12P 7/40; C12P 7/56; B01D 61/00; B01D 61/14; B01D 61/145; B01D 61/18; B01D 61/22; B01D 61/28; B01D 61/32; B01D 61/58; B01D 63/00; B01D 63/06; B01D 63/08; B01D 27/103; B01D 35/02; B01D 35/147; B01D 2313/083; B01D 29/00; B01D 29/01; B01D 29/03; B01D 35/00; B01D 35/005; B01D 37/02; B01D 37/00; B01D 37/04; B01D 37/045; B01D 39/10; B01D 61/16; B01D 65/00; B01D 65/08; B01D 2311/00; B01D 2311/02; B01D 2311/04; B01D 2311/25; B01D 2313/00; B01D 2313/18; B01D 2315/00
USPC ....... 210/637, 641, 739, 741, 744, 767, 790, 210/806, 167.05, 153, 132, 805, 85, 86, 210/97, 130, 141, 143
See application file for complete search history.

(56) References Cited

U.S. PATENT DOCUMENTS

| | | | |
|---|---|---|---|
| 6,139,746 A * | 10/2000 | Kopf | B01D 15/361 210/198.2 |
| 6,160,864 A | 12/2000 | Gou et al. | |
| 6,569,340 B2 | 5/2003 | Kopf | |
| 10,428,358 B2 | 10/2019 | Mimitsuka et al. | |
| 2002/0170859 A1 | 11/2002 | Kopf | |
| 2004/0137571 A1* | 7/2004 | Markussen | C07K 1/30 435/69.1 |
| 2011/0177551 A1 | 7/2011 | Mimitsuka et al. | |
| 2016/0168601 A1 | 6/2016 | Mimitsuka et al. | |
| 2018/0021737 A1 | 1/2018 | Banju et al. | |

FOREIGN PATENT DOCUMENTS

| | | | |
|---|---|---|---|
| JP | H04293522 A | 10/1992 | |
| JP | 2003512594 A | 4/2003 | |
| JP | S4641584 B2 | 3/2011 | |
| JP | 2013210239 A | 10/2013 | |
| JP | 2017159300 A | 9/2017 | |
| WO | 2010038613 A1 | 4/2010 | |
| WO | WO-2010038613 A1 * | 4/2010 | ............ C12M 29/18 |
| WO | 2017104259 A1 | 6/2017 | |

OTHER PUBLICATIONS

International Search Report issued in PCT/JP2018/022886, dated Sep. 18, 2018.
Written Opinion of the International Searching Authority issued in PCT/JP2018/022886, dated Sep. 18, 2018.

* cited by examiner

CONCENTRATION APPARATUS

CROSS REFERENCE TO RELATED APPLICATIONS

The present application is a continuation of International application No. PCT/JP2018/022886, filed Jun. 15, 2018, which claims priority to Japanese Patent Application No. 2017-130613, filed Jul. 3, 2017, the entire contents of each of which are incorporated herein by reference.

FIELD OF THE INVENTION

The present invention relates to a concentration apparatus that is of cross flow type and that obtains a concentrate by filtering a liquid containing a filtration object.

BACKGROUND OF THE INVENTION

A filtration apparatus disclosed in Patent Document (Japanese Unexamined Patent Application Publication No. 2013-210239), for example, has hitherto been known as a filtration apparatus for filtering a liquid containing a filtration object. In the filtration apparatus disclosed in Patent Document 1, the liquid containing the filtration object is supplied to flow along the surface of a filtration filter made of a hollow fiber membrane, for example, and a liquid (hereinafter referred to as a "filtrate") in which the filtration object is removed from the supplied liquid after passing through the filtration filter is collected.

According to the above-mentioned type of filtration apparatus, because the liquid containing the filtration object is supplied flows along the surface of the filtration filter, the filtration object trapped on the surface of the filtration filter is released from a trapped state by the flow of the liquid. Therefore, clogging of the filtration filter is suppressed, whereby the filtrate can be continuously collected for a longer time and filtration efficiency can be increased.

Furthermore, a concentrate containing the filtration object at a high concentration can be obtained with the aid of the above-mentioned type of filtration apparatus by circulating the liquid containing the filtration object to flow along the surface of the filtration filter many times, and by removing the filtrate having passed through the filtration filter. Hereinafter, the filtration apparatus aiming to obtain the concentrate is called a "concentration apparatus".

Patent Document 1: Japanese Unexamined Patent Application Publication No. 2013-210239

SUMMARY OF THE INVENTION

However, the filtration apparatus of the related art still has room for improvement in point of obtaining a concentrate having a higher concentration in a shorter time.

Accordingly, in solving the above-mentioned problem, an object of the present invention is to provide a concentration apparatus capable of obtaining a concentrate having a higher concentration in a shorter time.

To achieve the above-mentioned object, according to an embodiment of the present invention, there is provided a concentration apparatus being of a cross flow type and obtaining a concentrate by filtering a liquid containing a filtration object. Such a concentration apparatus includes a liquid tank storing a liquid containing a filtration object; a tubular member having first and second end portions disposed in the liquid tank, and forming a first circulation flow path between the first and second end portions; a circulation pump for supplying the liquid stored in the liquid tank to flow from the first end portion to the second end portion of the tubular member in a circulating manner; a filtration filter between the first end portion and the second end portion, the filtration filter including a metallic porous membrane sized to separate the filtration object from the liquid; a bypass pipe having first and second ends thereof connected to sidewalls of the tubular member so as to form a second circulation flow path between the first end portion and the second end portion of the tubular member, the second circulation flow path having a shorter path length than the first circulation flow path; a switching valve constructed to cause the liquid to flow in one of the first circulation flow path or the second circulation flow path; and a control unit controlling driving of the circulation pump and a switching operation of the switching valve.

With the concentration apparatus according to the present invention, a concentrate having a higher concentration can be obtained in a shorter time.

DETAILED DESCRIPTION OF THE PREFERRED EMBODIMENTS

Figure 1:
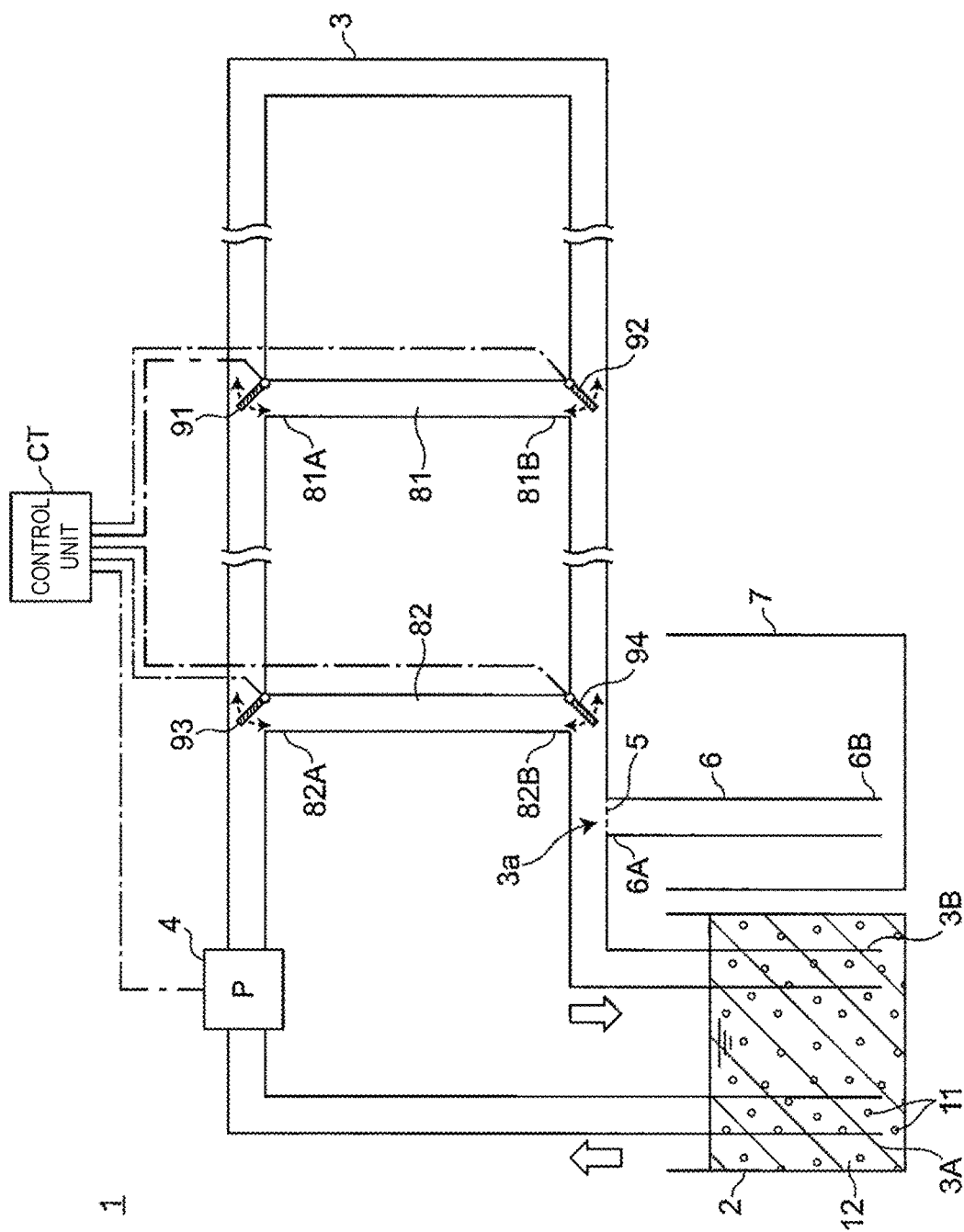
FIG. 1 is a diagrammatic illustration of a concentration apparatus according to Embodiment 1 of the present invention.

The inventors have attained the following novel knowledge as a result of intensive studies aiming to obtain a concentrate having a higher concentration in a shorter time.

The filtration apparatus of the related art can be utilized to obtain a concentrate, for example, by supplying a liquid stored in a liquid tank and containing a filtration object to flow in a circulation flow path with a circulation pump, removing a filtrate after filtering the liquid with a filtration filter disposed in the circulation flow path, and by returning the remaining liquid to the liquid tank. The liquid returned to the liquid tank is supplied again to flow in the circulation flow path with the circulation pump, and is returned to the liquid tank after the filtrate has been removed through the filtration with the filtration filter. By repeating the above operation, it is possible to remove a larger amount of the filtrate from the liquid containing the filtration object, and to obtain the concentrate having a higher concentration.

Furthermore, with the above-described constitution, the concentrate can be obtained in a shorter time, for example, by increasing an output of the circulation pump to raise a flow speed of the liquid, or by increasing an inner volume (length×opening area) of the circulation flow path to increase an amount of the liquid flowing in the circulation flow path.

However, for example, when the filtration object is a biological substance such as a cell, raising the flow speed of the liquid increases shearing force and frictional force applied to the biological substance, and increases stress acting on the biological substance. Furthermore, when the inner volume is increased by prolonging the circulation flow path, the stress acting on the biological substance is increased because the biological substance flows in the circulation flow path for a longer time. Thus, there is a limitation in raising the flow speed of the liquid or prolonging the circulation flow path for the purpose of obtaining the concentrate in a shorter time.

Moreover, because the amount of the liquid is reduced by removing the filtrate through the filtration filter from the liquid flowing in the circulation flow path, bubble mixing (i.e., mixing of bubbles into the liquid) may occur. The occurrence of the bubble mixing may, for example, adversely affect the pump operation and cause a significant variation in pressure of the liquid flowing in the circulation flow path. The bubble mixing is more likely to occur when the amount of the liquid (concentrate) in the liquid tank becomes, for example, not more than twice the inner volume of the circulation flow path. Therefore, it is desired to stop the filtration when the amount of the liquid in the liquid tank becomes not more than twice the inner volume of the circulation flow path. This gives rise to difficulty in obtaining the concentrate having a higher concentration. In particular, as the inner volume of the circulation flow path increases, the amount of the liquid in the liquid tank needs to be increased, and more difficulty arises in obtaining the concentrate having a higher concentration.

To cope with such a situation, the inventors have conceived a structure in which a bypass pipe is connected to sidewalls of a tubular member forming the circulation flow path, and a switching valve is disposed to switch a flow of the liquid flowing in the tubular member to flow through the bypass pipe. With that structure, the concentrate can be obtained in a shorter time by increasing the inner volume of the circulation flow path in an initial stage of the filtration. Furthermore, the circulation flow path can be shunt to give a shorter path length and to substantially reduce the inner volume of the circulation flow path by switching the switching valve at timing of, for example, the occurrence of the bubble mixing. As a result, the filtration can be continued while the occurrence of the bubble mixing is suppressed, and the concentrate having a higher concentration can be obtained. The inventors have made the following invention on the basis of the above-described novel knowledge.

The concentration apparatus according one embodiment of the present invention is of a cross flow type and obtains a concentrate by filtering a liquid containing a filtration object. The concentration apparatus includes a liquid tank storing a liquid containing the filtration object; a tubular member having first and second end portions disposed in the liquid tank, and forming a first circulation flow path between the first end portion and the second end portion; a circulation pump for supplying the liquid stored in the liquid tank to flow from the first end portion to the second end portion of the tubular member in a circulating manner; a filtration filter between the first end portion and the second end portion, the filtration filter including a metallic porous membrane sized to separate the filtration object from the liquid; a bypass pipe having first and second ends thereof connected to sidewalls of the tubular member so as to form a second circulation flow path between the first end portion and the second end portion of the tubular member, the second circulation flow path having a shorter path length than the first circulation flow path; a switching valve constructed to cause the liquid to flow in one of the first circulation flow path or the second circulation flow path; and a control unit controlling driving of the circulation pump and a switching operation of the switching valve.

With the above features, a concentrate having a higher concentration can be obtained in a shorter time.

The control unit may switch the switching valve to cause the liquid flowing in the tubular member to flow through the bypass pipe, when a remaining amount of the liquid stored in the liquid tank is reduced to a threshold or below. With that feature, the occurrence of the bubble mixing can be suppressed, and the concentrate having a higher concentration can be obtained in a shorter time.

Alternatively, the control unit may switch the switching valve to cause the liquid flowing in the tubular member to flow through the bypass pipe, when a pressure or a flow speed of the liquid flowing in the tubular member is reduced to a threshold or below. With that feature, the occurrence of the bubble mixing can be suppressed, and the concentrate having a higher concentration can be obtained in a shorter time.

With the progress of the filtration, the concentration of the concentrate flowing in the circulation flow path increases and the filtration object is more susceptible to stress because of more likely colliding against the other filtration objects or the sidewalls of the tubular member. To cope with the above point, the concentration apparatus may further include a filtrate pump promoting part of the liquid flowing in the tubular member to pass through the filtration filter, and the control unit may reduce driving force of the filtrate pump when the switching valve is switched to cause the liquid flowing in the tubular member to flow through the bypass pipe. With those features, the stress acting on the filtration object can be reduced because a filtration rate (speed of concentration) is set lower than that in an initial stage.

The bypass pipe may include a first bypass pipe and a second bypass pipe, the second bypass pipe shunting the circulation flow path to give a shorter path length than a path formed by the first bypass pipe, the switching valve may be switched to cause the liquid flowing in the tubular member to flow through the first bypass pipe or the second bypass pipe, and the control unit may drive the filtrate pump with first driving force when the switching valve is switched to cause the liquid flowing in the tubular member to flow through the first bypass pipe, and may drive the filtrate pump with second driving force smaller than the first drive force when the switching valve is switched to cause the liquid flowing in the tubular member to flow through the second bypass pipe. With those features, since the filtration rate is gradually (stepwisely) slowed down, it is possible to not only obtain the concentrate having a higher concentration in a shorter time, but also to reduce the stress acting on the filtration object.

The control unit may switch the switching valve to make a time during which the liquid flows through the second bypass pipe longer than a time during which the liquid flows through the first bypass pipe. With that feature, the stress acting on the filtration object can be further reduced because of reduction in a speed of the concentrate flowing in the second bypass pipe in which the concentration of the concentrate is higher than that of the concentrate flowing in the first bypass pipe.

The concentration apparatus may further include a bypass-pipe filtration filter disposed in a sidewall of the bypass pipe and including a metallic porous membrane for filtration to separate the filtration object. With that feature, for example, even when the filtration filter is clogged, the filtration can be continued with the presence of the bypass-pipe filtration filter. Hence the concentrate having an even higher concentration can be obtained in a shorter time.

The bypass pipe may have a smaller inner diameter than the tubular member. With that feature, the concentrate having an even higher concentration can be obtained because the inner volume of the circulation flow path is further reduced. In addition, the stress acting on the filtration object can be reduced because the filtration rate is made lower than that in the initial stage.

In the above case, on the upstream side of the bypass pipe in a flow direction of the liquid, when the liquid is going to flow from the tubular member having a relatively large inner diameter to the bypass pipe having a relatively small inner diameter, a flow of the liquid is impeded and pressure of the liquid is difficult to control. In consideration of the above point, the filtration filter is preferably disposed downstream of the bypass pipe in the flow direction of the liquid. With that feature, the liquid can be more stably filtered (concentrated) with the filtration filter.

The embodiments of the present invention will be described below with reference to the drawings. It is to be noted that the present invention is not restricted by the embodiments.

Embodiment 1

A concentration apparatus according to Embodiment 1 is a concentration apparatus that is of cross flow type and that obtains a concentrate by filtering a liquid containing a filtration object. FIG. 1 is a diagrammatic illustration of the concentration apparatus according to Embodiment 1.

As illustrated in FIG. 1, the concentration apparatus 1 according to Embodiment 1 includes a liquid tank 2 and a tubular member 3.

The liquid tank 2 is a container that stores a liquid 12 containing a filtration object 11. The liquid tank 2 may be a container opened at an upper surface as illustrated in FIG. 1, or an enclosed container.

In this Embodiment 1, the filtration object 11 is a biological substance contained in a liquid. In this Description, the term "biological substance" implies a substance derived from living things, such as a cell (eukaryote), bacteria (eubacteria), a virus, etc. The cell (eukaryote) includes, for example, an ovum, a sperm, an induced pluripotent stem cell (iPS cell), an ES cell, a stem cell, a mesenchymal stem cell, a mononuclear cell, a single cell, a cell mass, a floating cell, an adhesive cell, a nerve cell, a leucocyte, a lymphocyte, a regenerative medicine cell, an autologous cell, a cancer cell, a circulating tumor cell (CTC), HL-60, HELA, and fungi. The bacteria (eubacteria) include, for example, *E. coli* and *Mycobacterium tuberculosis*.

The tubular member 3 forms a circulation flow path in which the liquid 12 flows. The tubular member 3 is a pipe having a circular, elliptic or rectangular sectional shape, for example. Materials of the tubular member 3 are, for example, stainless steel, silicon resin, PVDF (Teflon: registered trade mark), vinyl chloride, glass, and butadiene-free resin. A coating material may be coated over an inner surface of the tubular member 3 such that the filtration object 11 is harder to adhere to the inner surface.

Both end portions of the tubular member 3 are arranged in the liquid tank 2. In other words, one end portion 3A and the other end portion 3B of the tubular member 3 are both arranged in the liquid tank 2.

A circulation pump 4 is attached to the tubular member 3 and supplies the liquid 12, which is stored in the liquid tank 2, to flow from the one end portion 3A to the other end portion 3B of the tubular member 3 in a circulating manner. With driving of the circulation pump 4, the liquid 12 stored in the liquid tank 2 flows from the one end portion 3A to the other end portion 3B of the tubular member 3 and returns to the liquid tank 2. With the continued driving of the circulation pump 4, the liquid 12 having been returned to the liquid tank 2 flows from the one end portion 3A to the other end portion 3B of the tubular member 3 and returns to the liquid tank 2 again.

Figure 2:
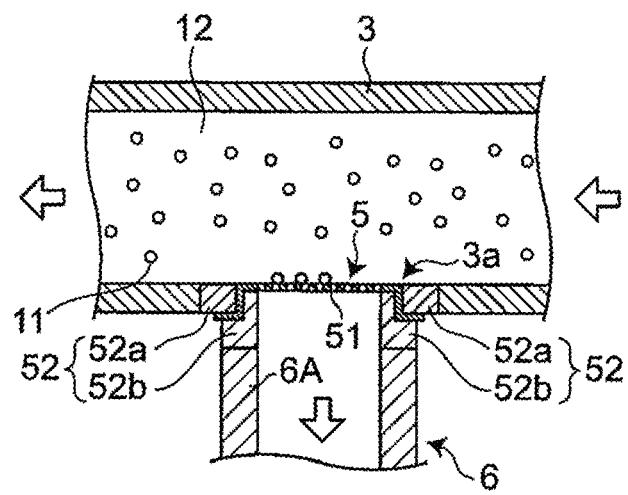
FIG. 2 is a sectional view representing a structure of a portion including a filtration filter and the surroundings in the concentration apparatus illustrated in FIG. 1.

A filtration filter 5 for filtration to separate the filtration object 11 is disposed in a sidewall of the tubular member 3. As illustrated in FIG. 2, the filtration filter 5 is attached to a through-hole 3a, which is formed in part of the sidewall of the tubular member 3, to be positioned along the sidewall.

The filtration filter 5 includes a metallic porous membrane 51 for filtration to separate the filtration object 11, and a frame member 52 holding an outer peripheral portion of the metallic porous membrane 51.

Figure 3:
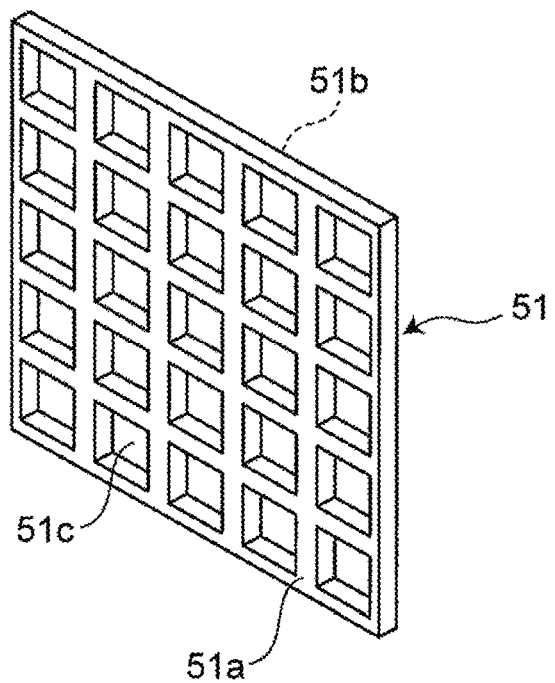
FIG. 3 is an enlarged perspective view of part of a metallic porous membrane in the filtration filter illustrated in FIG. 2.

The metallic porous membrane 51 is arranged to lie along a flow direction of the liquid 12. In this Embodiment 1, the metallic porous membrane 51 is a porous membrane for separating the biological substance. As illustrated in FIG. 3, the metallic porous membrane 51 has a first principal surface 51a and a second principal surface 51b opposing to each other. Many through-holes 51c penetrating from the first principal surface 51a to the second principal surface 51b are formed in the metallic porous membrane 51. The through-holes 51c are to separate the biological substance from the liquid 12. The shape and size of the through-holes 51c are set as appropriate depending on the shape and size of the biological substance. The through-holes 51c are arranged, for example, at equal intervals or periodically. The shape of the through-holes 51c is, for example, square when looking at the through-holes 51c from the side facing the first principal surface 51a or the second principal surface 51b of the metallic porous membrane 51. The size of the through-holes 51c is, for example, 0.1 μm or more and 500 μm or less in length and 0.1 μm or more and 500 μm or less in width. The interval between the through-holes 51c is, for example, 1 time or more and 10 times or less, more preferably 3 times or less, an opening size of each through-hole 51c. An opening ratio of the through-holes 51c in the metallic porous membrane 51 is, for example, 10% or more.

Materials of the metallic porous membrane 51 are, for example, gold, silver, copper, platinum, nickel, stainless steel, palladium, titanium, cobalt, alloys of those elements, or oxides of those elements. The size of the metallic porous membrane 51 is, for example, 6 mm in diameter and 0.1 μm or more and 100 µm or less, preferably 0.1 µm or more and 50 µm or less, in thickness. The external form of the metallic porous membrane 51 is, for example, circular, elliptic, or polygonal. In this Embodiment 1, the external form of the metallic porous membrane 51 is square. The through-holes 51c may or may not be formed in an outer peripheral portion of the metallic porous membrane 51.

The frame member 52 includes a first frame member 52a and a second frame member 52b. The first frame member 52a and the second frame member 52b are each formed in a ring shape (e.g., a circular ring shape). The frame member 52 holds the metallic porous membrane 51 by sandwiching the outer peripheral portion of the metallic porous membrane 51 between the first frame member 52a and the second frame member 52b. Materials of the first frame member 52a and the second frame member 52b are, for example, metals such as duralumin and aluminum, and resins such as polyethylene, polystyrene, polypropylene, polycarbonate, polyacetal, and polyether imide.

As illustrated in FIG. 2, one end portion 6A of a filtrate discharge pipe 6 is connected to the second frame member 52b, the filtrate discharge pipe 6 forming a filtrate flow path through which a filtrate (waste liquid) after having passed through the filtration filter 5 flows. As illustrated in FIG. 1, the other end portion 6B of the filtrate discharge pipe 6 is arranged in a filtrate tank 7. The filtrate flowing from the one end portion 6A of the filtrate discharge pipe 6 to the other end portion 6B is stored into the filtrate tank 7. The filtrate tank 7 may be a container opened at an upper surface as illustrated in FIG. 1, or an enclosed container.

Furthermore, as illustrated in FIG. 1, a first bypass pipe 81 and a second bypass pipe 82, each shunting the circulation flow path to give a shorter path length, are connected to sidewalls of the tubular member 3. Both end portions of each of the first bypass pipe 81 and the second bypass pipe 82 are connected to the tubular member 3. The second bypass pipe 82 is connected to the tubular member 3 in a fashion of shortening a length of the circulation flow path in comparison with the first bypass pipe 81.

In this Embodiment 1, the first bypass pipe 81 and the second bypass pipe 82 are arranged downstream of the circulation pump 4 in the flow direction of the liquid 12 and upstream of the filtration filter 5 in the flow direction of the liquid 12. The first bypass pipe 81 and the second bypass pipe 82 are each a pipe of which sectional shape and material are similar to those of the tubular member 3.

A first valve 91 is disposed in a joint region between the tubular member 3 and one end portion 81A of the first bypass pipe 81. A second valve 92 is disposed in a joint region between the tubular member 3 and the other end portion 81B of the first bypass pipe 81. In this Embodiment 1, the first valve 91 and the second valve 92 constitute a switching valve for switching the circulation flow path such that the liquid 12 flowing in the tubular member 3 flows through the first bypass pipe 81.

A third valve 93 is disposed in a joint region between the tubular member 3 and one end portion 82A of the second bypass pipe 82. A fourth valve 94 is disposed in a joint region between the tubular member 3 and the other end portion 82B of the second bypass pipe 82. In this Embodiment 1, the third valve 93 and the fourth valve 94 constitute a switching valve for switching the circulation flow path such that the liquid 12 flowing in the tubular member 3 flows through the second bypass pipe 82.

The circulation pump 4, the first valve 91, the second valve 92, the third valve 93, and the fourth valve 94 are each electrically connected to a control unit CT wirelessly or by wire. The control unit CT controls driving of the circulation pump 4 and switching operations of the first valve 91, the second valve 92, the third valve 93, and the fourth valve 94.

Figure 4:
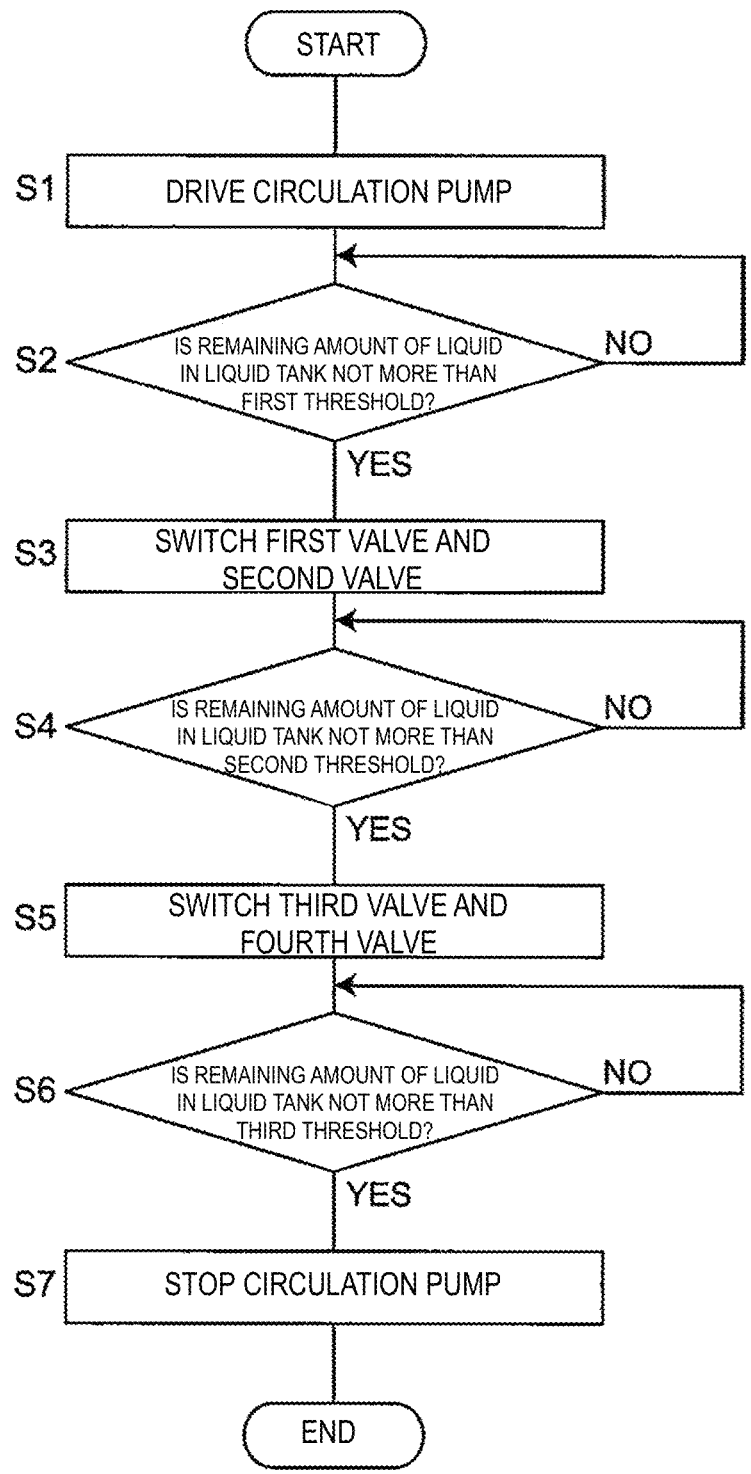
FIG. 4 is a flowchart representing an operation of the concentration apparatus, illustrated in FIG. 1, to obtain a concentrate with filtration performed on a filtration object.
Figure 5:
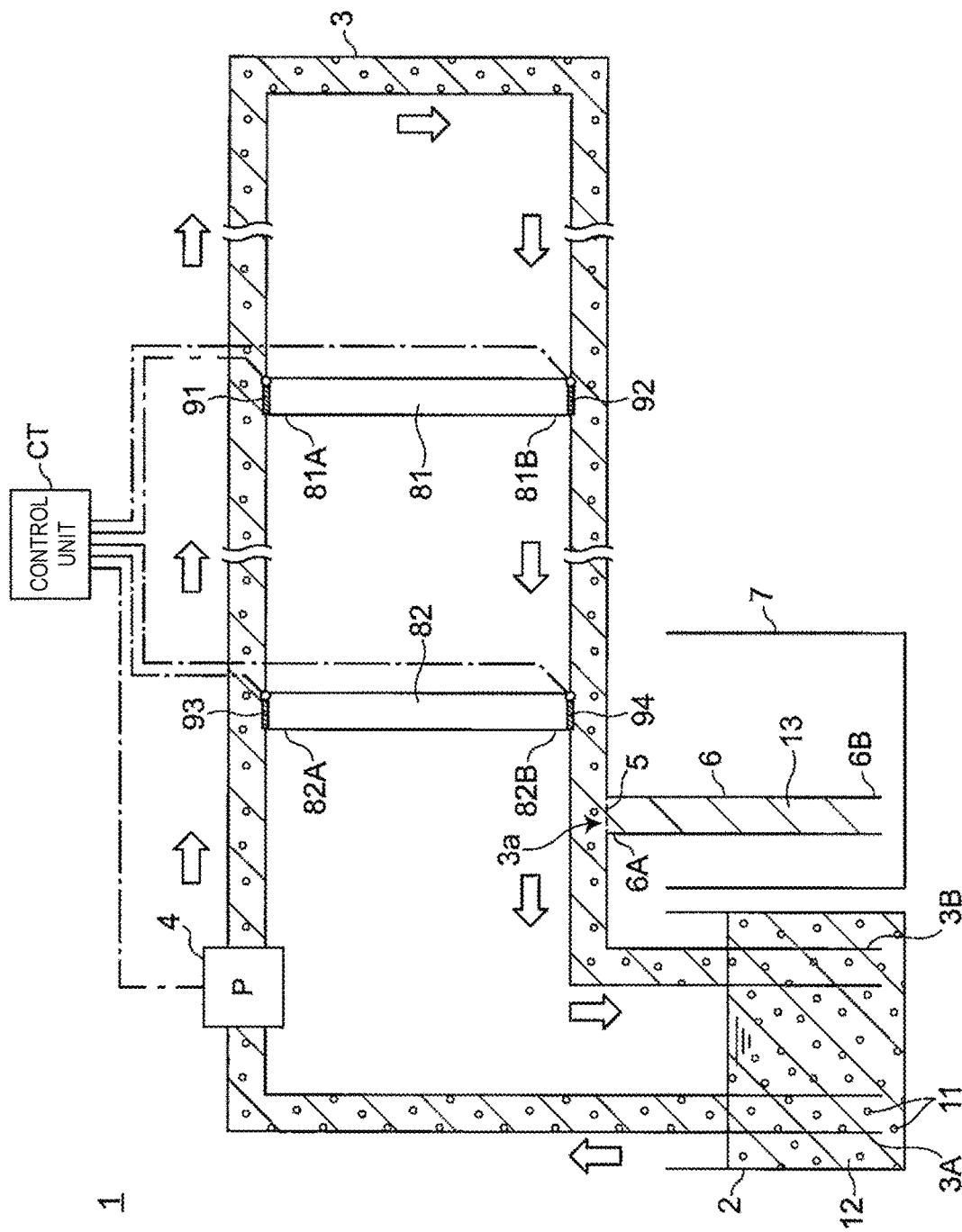
FIG. 5 is a diagrammatic illustration representing an operation of the concentration apparatus, illustrated in FIG. 1, to obtain the concentrate by the filtration performed on the filtration object.
Figure 6:
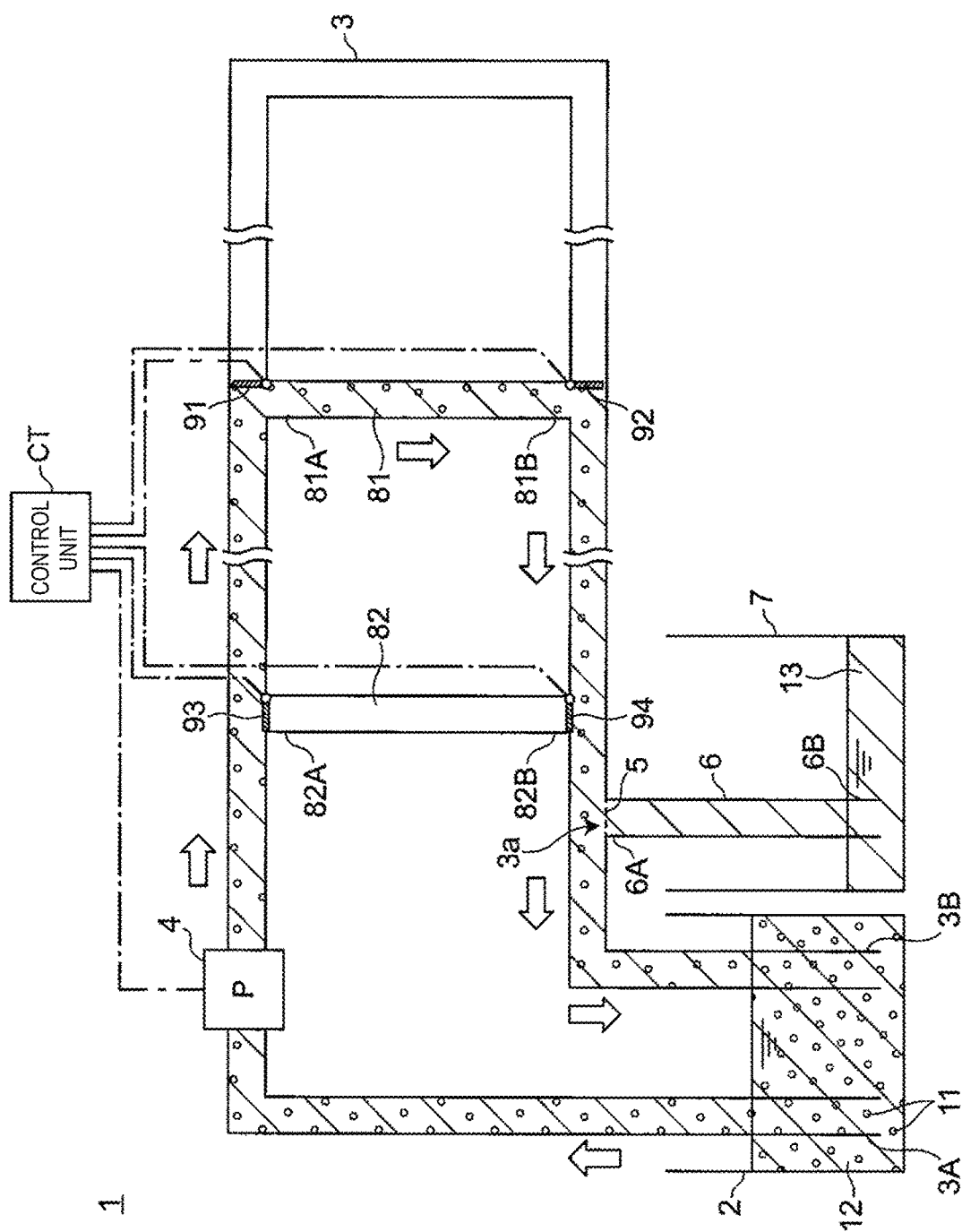
FIG. 6 is a diagrammatic illustration representing an operation subsequent to the operation illustrated in FIG. 5.
Figure 7:
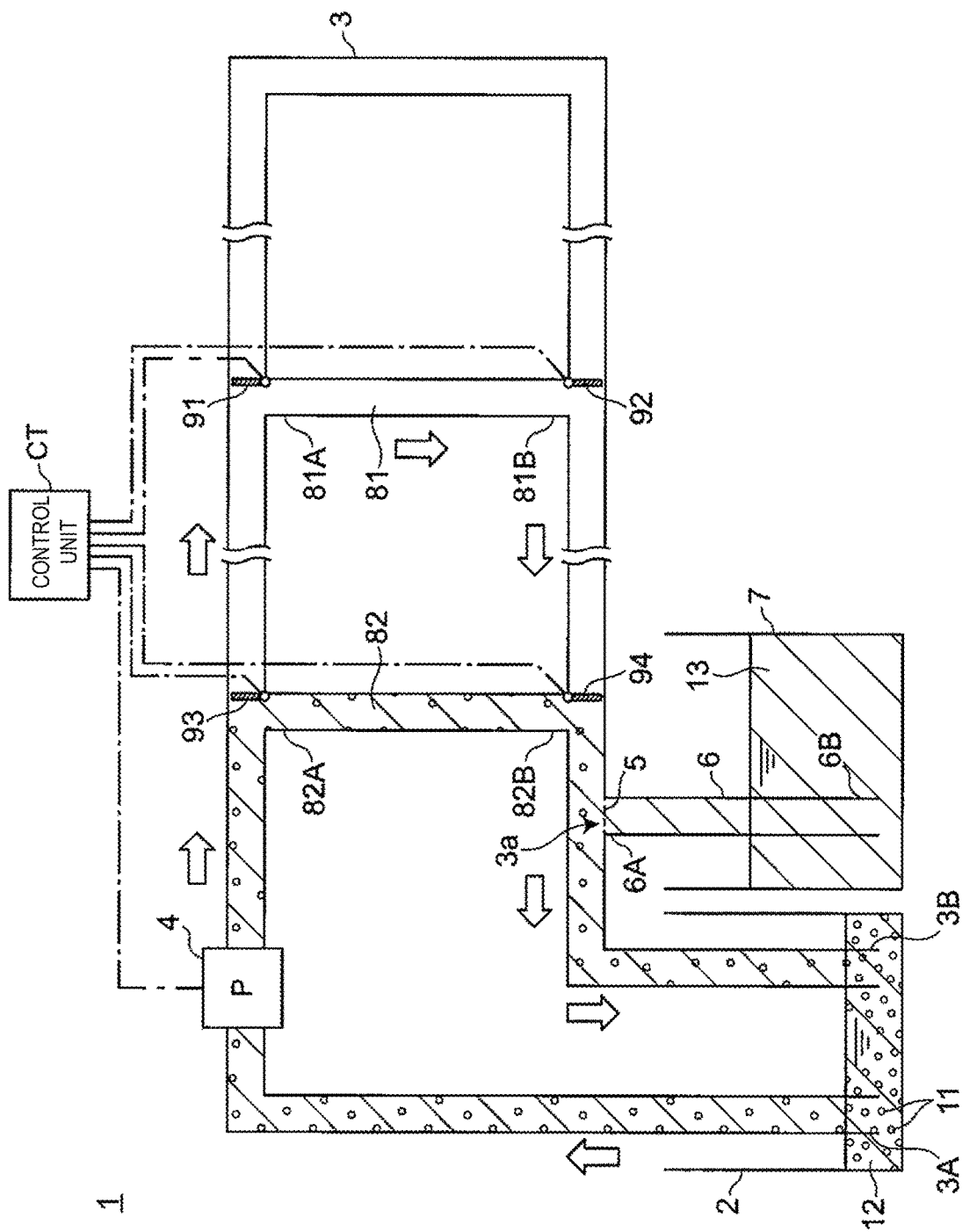
FIG. 7 is a diagrammatic illustration representing an operation subsequent to the operation illustrated in FIG. 6.

An operation of the concentration apparatus 1 to obtain a concentrate with filtration performed on the filtration object 11 will be described below with reference to FIGS. 4 to 7. FIG. 4 is a flowchart representing the operation of the concentration apparatus 1 to obtain the concentrate by the filtration performed on the filtration objects. FIGS. 5 to 7 are each a diagrammatic illustration representing the operation of the concentration apparatus 1 to obtain the concentrate by the filtration performed on the filtration object 11.

In response to a user's operation of, for example, pressing a start button (not illustrated), the control unit CT drives the circulation pump 4 (step S1). With the driving of the circulation pump 4, as illustrated in FIG. 5, the liquid 12 in the liquid tank 2 is caused to flow from the one end portion 3A of the tubular member 3 to the other end portion 3B. At this time, an overall length of the tubular member 3 from the one end portion 3A to the other end portion 3B serves as the circulation flow path.

Part of the liquid 12 flowing in the tubular member 3 passes through the filtration filter 5 and is stored as the filtrate into the filtrate tank 7 through the filtrate discharge pipe 6. The filtration object 11 contained in the liquid 12 remains in the tubular member 3 after the filtration by the filtration filter 5, flows toward the other end portion 3B of the tubular member 3 in accordance with the flow of the liquid 12, and is stored into the liquid tank 2. As a result, the concentration of the filtration object 11, which is contained in the liquid 12, increases in the liquid tank 2.

Then, if a remaining amount of the liquid 12 (concentrate) in the liquid tank 2 is reduced to a first threshold or below, the control unit CT switches the first valve 91 and the second valve 92, as illustrated in FIG. 6, such that the liquid 12 flowing from the one end portion 3A of the tubular member 3 advances toward the other end portion 3B of the tubular member 3 through the first bypass pipe 81 (steps S2 and S3). Thus, the circulation flow path is shortened by shunting with the first bypass pipe 81. The remaining amount of the liquid 12 in the liquid tank 2 can be measured, for example, by attaching a water level indicator (not illustrated) to the liquid tank 2.

Part of the liquid 12 flowing in the circulation flow path shortened by the shunting with the first bypass pipe 81 passes through the filtration filter 5 and is stored as the filtrate into the filtrate tank 7 through the filtrate discharge pipe 6. The filtration object 11 contained in the liquid 12 remains in the tubular member 3 after the filtration by the filtration filter 5, flows toward the other end portion 3B of the tubular member 3 in accordance with the flow of the liquid 12, and is stored into the liquid tank 2. As a result, the concentration of the filtration object 11, which is contained in the liquid 12, further increases in the liquid tank 2.

Then, if the remaining amount of the liquid 12 in the liquid tank 2 is reduced to a second threshold or below, the control unit CT switches the third valve 93 and the fourth valve 94, as illustrated in FIG. 7, such that the liquid 12 flowing from the one end portion 3A of the tubular member 3 advances toward the other end portion 3B of the tubular member 3 through the second bypass pipe 82 (steps S4 and S5). Thus, the circulation flow path is further shortened by shunting with the second bypass pipe 82.

Part of the liquid 12 flowing in the circulation flow path further shortened by the shunting with the second bypass pipe 82 passes through the filtration filter 5 and is stored as the filtrate into the filtrate tank 7 through the filtrate discharge pipe 6. The filtration object 11 contained in the liquid 12 remains in the tubular member 3 after the filtration by the filtration filter 5, flows toward the other end portion 3B of the tubular member 3 in accordance with the flow of the liquid 12, and is stored into the liquid tank 2. As a result, the concentration of the filtration object 11, which is contained in the liquid 12, still further increases in the liquid tank 2.

Then, if the remaining amount of the liquid 12 in the liquid tank 2 is reduced to a third threshold or below, the control unit CT stops the driving of the circulation pump 4 (steps S6 and S7). Thus, the concentrate having a higher concentration can be obtained in the liquid tank 2.

In the concentration apparatus 1 according to Embodiment 1, the first to fourth valves 91 to 94 are switched such that the liquid 12 flowing in the tubular member 3 flows through the first bypass pipe 81 or the second bypass pipe 82. With that feature, in an initial stage of the filtration, the circulation flow path has a larger inner volume, and the concentrate can be obtained in a shorter time. Furthermore, the circulation flow path can be shortened and the inner volume of the circulation flow path can be reduced by switching the first to fourth valves 91 to 94. As a result, the filtration can be continued while the occurrence of the bubble mixing is suppressed, and the concentrate having a higher concentration can be obtained.

When the filtration object 11 is cells, the cells are apt to undergo shearing force while the liquid 12 containing the cells flows in the circulation flow path with a small diameter. Therefore, if the concentration apparatus has a structure in which the cells flow only in the circulation flow path, stress attributable to the shearing force applied to the cells increases.

On the other hand, in the concentration apparatus 1 according to Embodiment 1, the circulation flow paths defined by switching the first to fourth valves 91 to 94 are all formed as paths including the liquid tank 2 because of aiming to concentrate the liquid 12 stored in the liquid tank 2. With that feature, the liquid 12 containing the cells always flow in the circulation flow path to circulate through the liquid tank 2. Therefore, the stress attributable to the shearing force applied to the cells can be temporarily relieved in the liquid tank 2. As a result, an adverse effect such as retarding cell proliferation in subculture of the cells can be suppressed.

The present invention is not limited to the above embodiment, and it can be implemented in other various embodiments. For example, while the control unit CT has been described above as controlling the first to fourth valves 91 to 94 to be switched when the remaining amount of the liquid 12 stored in the liquid tank 2 is reduced to the first or second threshold or below, the present invention is not limited to such a case. When the bubble mixing occurs, for example, the pressure or the flow speed of the liquid 12 flowing in the tubular member 3 reduces abruptly. In other words, the timing of the occurrence of the bubble mixing can be estimated on the basis of the pressure or the flow speed of the liquid 12 flowing in the tubular member 3. Accordingly, the control unit CT may control the first to fourth valves 91 to 94 to be switched when the pressure or the flow speed of the liquid 12 flowing in the tubular member 3 is reduced to a threshold or below. That control can also suppress the occurrence of the bubble mixing and produce the concentrate having a higher concentration in a shorter time. The pressure or the flow speed of the liquid 12 flowing in the tubular member 3 can be measured, for example, by attaching a pressure gauge or a flowmeter to the tubular member 3.

Furthermore, the remaining amount of the liquid 12 stored in the liquid tank 2 is correlated to an amount of the filtrate in the filtrate tank 7. Therefore, the control unit CT may control the first to fourth valves 91 to 94 to be switched when the amount of the filtrate in the filtrate tank 7 is increased to a threshold or above. That control can also suppress the occurrence of the bubble mixing and produce the concentrate having a higher concentration in a shorter time.

The remaining amount of the liquid 12 stored in the liquid tank 2 is further correlated to an output or a driving time of the circulation pump 4. Therefore, the control unit CT may control the first to fourth valves 91 to 94 to be switched on the basis of the output or the driving time of the circulation pump 4. That control can also suppress the occurrence of the bubble mixing and produce the concentrate having a higher concentration in a shorter time.

While, in the above description, the filtration filter 5 is arranged downstream of both the first bypass pipe 81 and the second bypass pipe 82 in the flow direction of the liquid 12, the present invention is not limited to such a case. For example, the filtration filter 5 may be arranged upstream of both the first bypass pipe 81 and the second bypass pipe 82 in the flow direction of the liquid 12.

While, in the above description, the filtration is started in a state in which, as illustrated in FIG. 5, the first bypass pipe 81 and the second bypass pipe 82 are closed by the first to fourth valves 91 to 94, the present invention is not limited to such a case. For example, the filtration may be started in a state in which the first bypass pipe 81 and the second bypass pipe 82 are opened (e.g., in a state illustrated in FIG. 1). In this case, the inner volume of the circulation flow path is a total of the inner volumes of the tubular member 3, the first bypass pipe 81, and the second bypass pipe 82. Accordingly, the inner volume of the circulation flow path is increased, whereby the concentrate can be obtained in a shorter time.

While, in the above description, two bypass pipes (i.e., the first bypass pipe 81 and the second bypass pipe 82) are connected to the tubular member 3, the present invention is not limited to such a case. For example, one or three or more bypass pipes may be connected to the tubular member 3. Thus, it is just required that at least one bypass pipe is connected to the tubular member 3.

While, in the above description, four valves (i.e., the first to fourth valves 91 to 94) are disposed as the switching valves, the present invention is not limited to such a case. The switching valves are just required to be switchable so as to cause the liquid 12 flowing in the tubular member 3 to flow through the bypass pipe.

Embodiment 2

Figure 8:
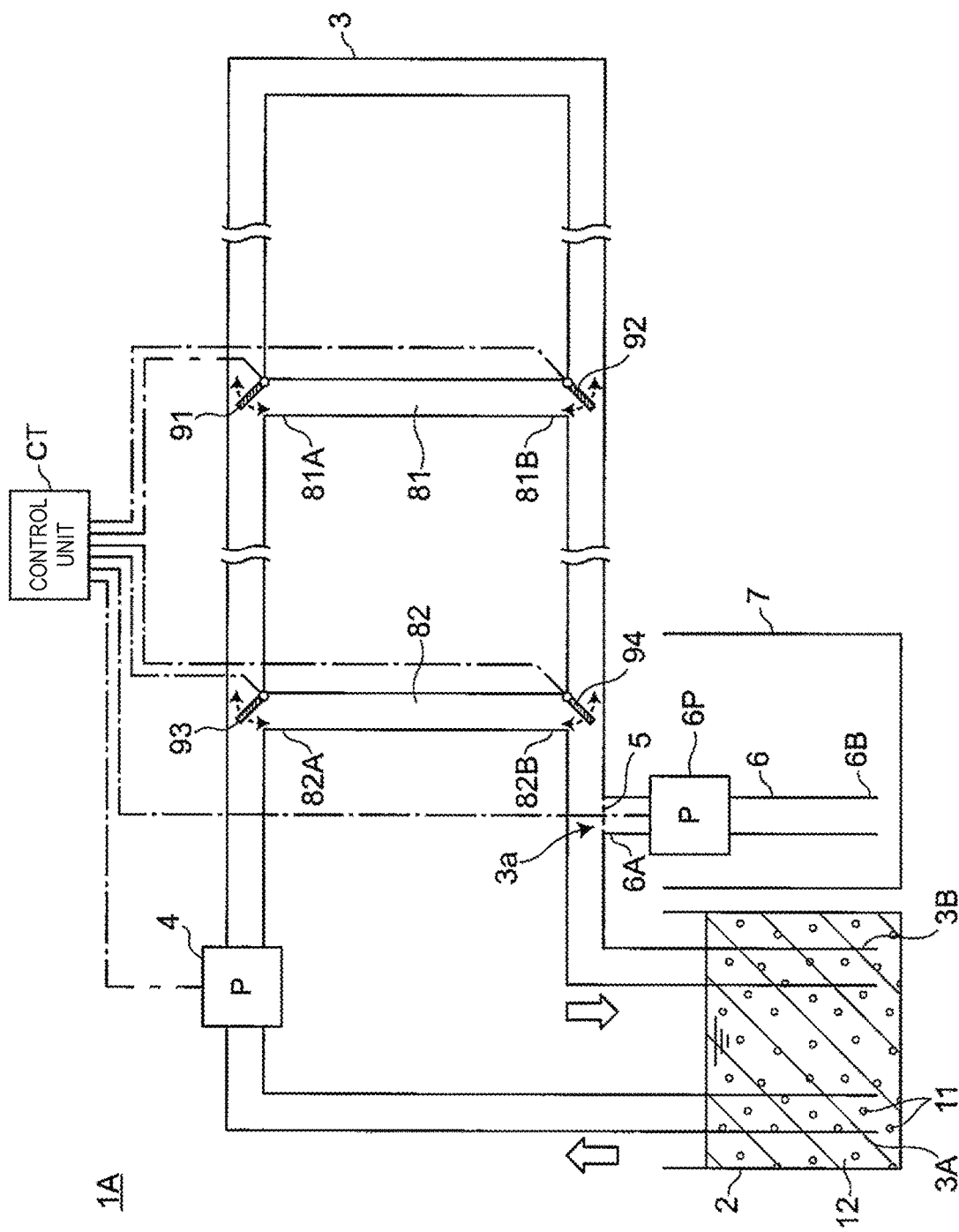
FIG. 8 is a diagrammatic illustration of a concentration apparatus according to Embodiment 2 of the present invention.

FIG. 8 is a diagrammatic illustration of a concentration apparatus 1A according to Embodiment 2 of the present invention.

The concentration apparatus 1A according to Embodiment 2 is different from the concentration apparatus 1 according to Embodiment 1 in that a filtrate pump 6P is disposed in the filtrate discharge pipe 6.

The filtrate pump 6P is to promote part of the liquid 12 flowing in the tubular member 3 to pass through the filtration filter 5. The filtrate pump 6P is electrically connected to the control unit CT wirelessly or by wire.

With the progress of the filtration, the filtrate 13 is removed from the liquid 12 and the concentration of the filtration object 11 in the liquid 12 flowing in the circulation flow path increases. Therefore, the filtration object is more likely to collide against the other filtration objects or the sidewalls of the tubular member 3 and is more susceptible to stress.

To avoid the above problem, when the first valve 91 and the second valve 92 are switched to cause the liquid flowing in the tubular member 3 to flow through the first bypass pipe 81, the control unit CT controls the filtrate pump 6P to be driven by smaller driving force, i.e., first driving force, than that before the switching. Furthermore, when the third valve 93 and the fourth valve 94 are switched to cause the liquid flowing in the tubular member 3 to flow through the second bypass pipe 82, the control unit CT controls the filtrate pump 6P to be driven by second driving force smaller than the first driving force.

With the concentration apparatus 1A according to Embodiment 2, since a filtration rate (speed of concentration) is gradually (stepwisely) slowed down, it is possible to not only obtain the concentrate having a higher concentration in a shorter time, but also to reduce the stress acting on the filtration object 11.

Alternatively, the control unit CT may control the first to fourth valves 91 to 94 to be switched such that a time during which the liquid 12 flows through the second bypass pipe 82 is longer than a time during which the liquid 12 flows through the first bypass pipe 81. With such control, since a speed of the concentrate flowing through the second bypass pipe 82 and having a higher concentration than that flowing through the first bypass pipe 81 is slowed down, the stress acting on the filtration object can be further reduced.

Embodiment 3

Figure 9:
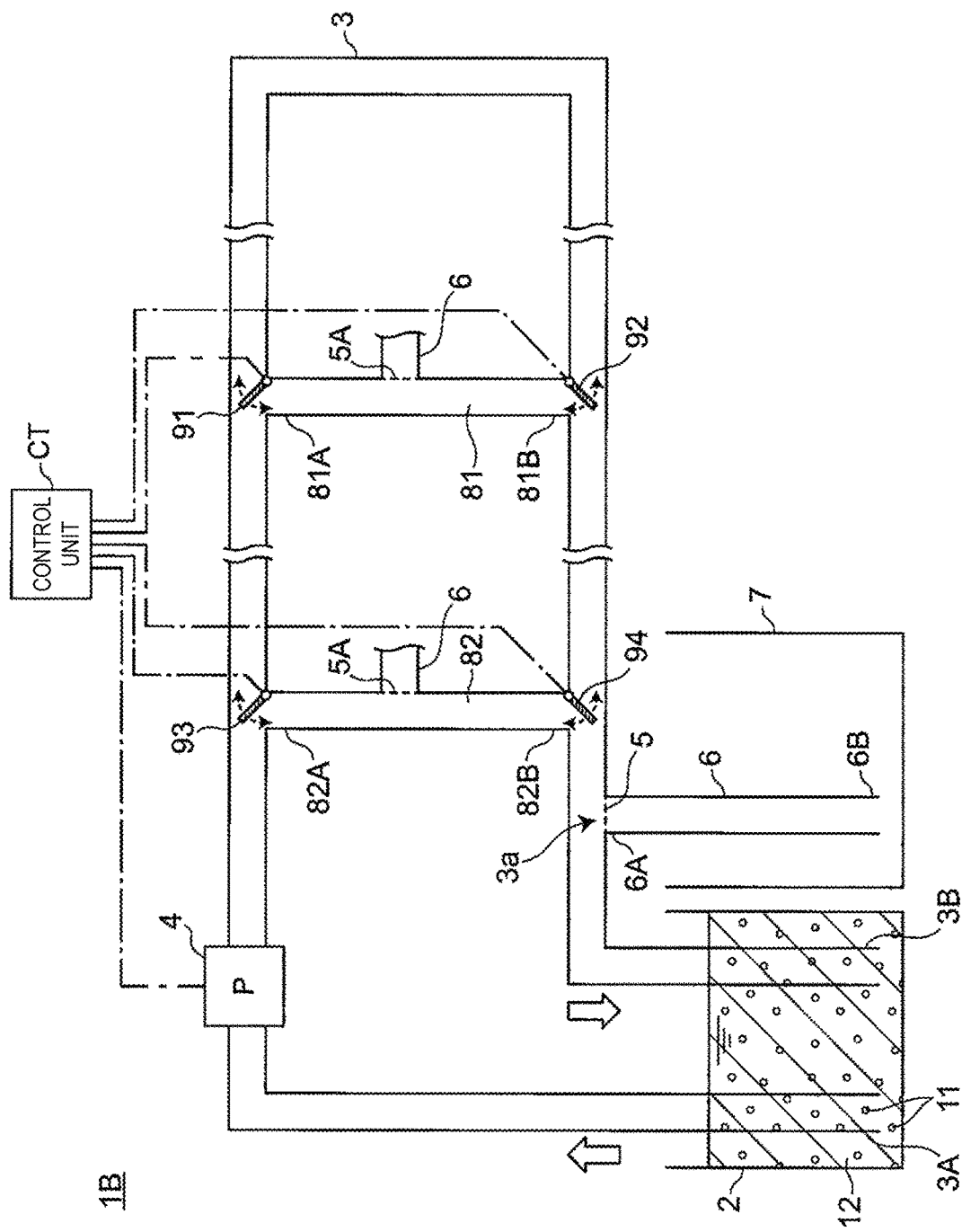
FIG. 9 is a diagrammatic illustration of a concentration apparatus according to Embodiment 3 of the present invention.

FIG. 9 is a diagrammatic illustration of a concentration apparatus 1B according to Embodiment 3 of the present invention.

The concentration apparatus 1B according to Embodiment 3 is different from the concentration apparatus 1 according to Embodiment 1 in that a bypass-pipe filtration filter 5A is disposed in each of the first bypass pipe 81 and the second bypass pipe 82.

In this Embodiment 3, the bypass-pipe filtration filter 5A has a similar structure to that of the above-described filtration filter. More specifically, the bypass-pipe filtration filter 5A includes the metallic porous membrane 51 illustrated in FIG. 2. The filtrate having passed through the bypass-pipe filtration filter 5A is stored into the filtrate tank 7 through a filtrate discharge pipe 6.

With the concentration apparatus 1B according to Embodiment 3, even when the filtration filter 5 is clogged, the filtration can be continued with the presence of the bypass-pipe filtration filter 5A. Hence the concentrate having an even higher concentration can be obtained in a shorter time.

Although the first to fourth valves 91 to 94 are switched at the timing of the occurrence of the bubble mixing in the above-described Embodiment 1, the first to fourth valves 91 to 94 may be switched at the timing of the occurrence of clogging of the filtration filter 5 in this Embodiment 3. Such switching suppresses continuation of the filtration in a state of the filtration filter 5 being clogged. As a result, the filtration object can be avoided from undergoing stress upon contact between the filtration object adhering to the filtration filter 5 and the other filtration objects.

For example, when the filtration filter 5 is clogged, the pressure of the filtrate 13 flowing in the filtrate discharge pipe 6 reduces. In other words, the timing of clogging of the filtration filter 5 can be estimated on the basis of the pressure of the filtrate 13 flowing in the filtrate discharge pipe 6. Thus, for example, a pressure gauge (not illustrated) may be attached to the filtrate discharge pipe 6, and the control unit CT may control the first to fourth valves 91 to 94 to be switched in accordance with the pressure detected by the pressure gauge.

In another example, a CCD camera (not illustrated) may be attached at a position facing the filtration filter 5, and the control unit CT may determine the clogging of the filtration filter 5 on the basis of an image taken by the CCD camera and control the first to fourth valves 91 to 94 to be switched in accordance with the result of the determination.

Embodiment 4

Figure 10:
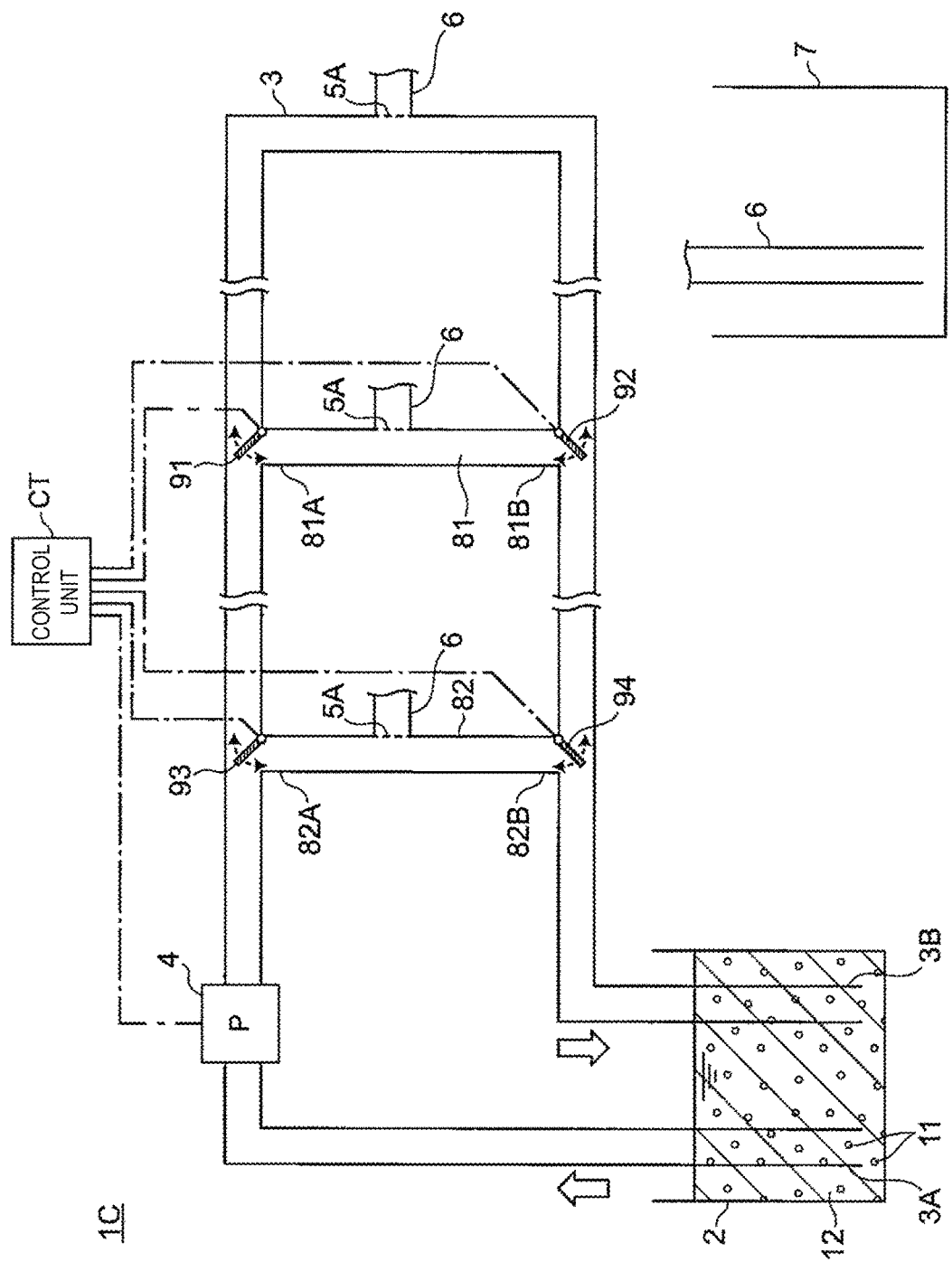
FIG. 10 is a diagrammatic illustration of a concentration apparatus according to Embodiment 4 of the present invention.

FIG. 10 is a diagrammatic illustration of a concentration apparatus 1C according to Embodiment 4 of the present invention.

The concentration apparatus 1C according to Embodiment 4 is different from the concentration apparatus 1B according to Embodiment 3 in that the filtration filter 5 is disposed in part of the tubular member 3, the part being positioned in parallel to the first bypass pipe 81.

In this Embodiment 4, when the filtration filter 5 disposed in the tubular member 3 is clogged, the control unit CT controls the first valve 91 and the second valve 92 to be switched such that the liquid 12 flows through the first bypass pipe 81. Moreover, when the bypass-pipe filtration filter 5A disposed in the first bypass pipe 81 is clogged, the control unit CT controls the third valve 93 and the fourth valve 94 to be switched such that the liquid 12 flows through the second bypass pipe 82.

With the concentration apparatus 1C according to this Embodiment 4, even when the filtration filter 5 is clogged, the filtration can be continued with the presence of the bypass-pipe filtration filter 5A. Hence the concentrate having an even higher concentration can be obtained in a shorter time.

Embodiment 5

Figure 11:
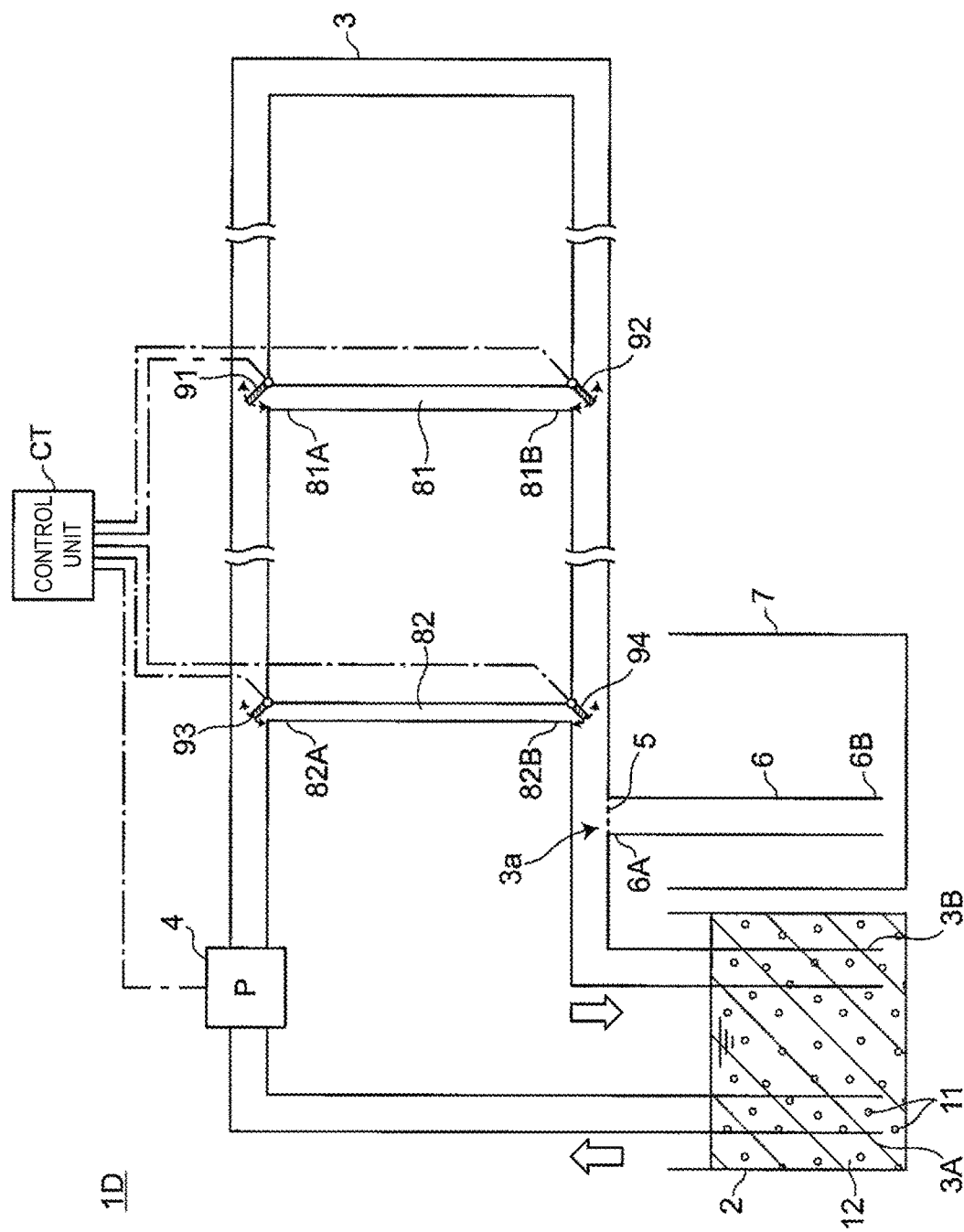
FIG. 11 is a diagrammatic illustration of a concentration apparatus according to Embodiment 5 of the present invention.

FIG. 11 is a diagrammatic illustration of a concentration apparatus 1D according to Embodiment 5 of the present invention.

The concentration apparatus 1D according to Embodiment 5 is different from the concentration apparatus 1 according to Embodiment 1 in that an inner diameter (opening area) of the first bypass pipe 81 is smaller than an inner diameter of the tubular member 3 and an inner diameter of the second bypass pipe 82 is smaller than the inner diameter of the first bypass pipe 81.

With the concentration apparatus 1D according to this Embodiment 5, the concentrate having an even higher concentration can be obtained by further reducing the inner volume of the circulation flow path. In addition, the stress acting on the filtration object can be reduced by slowing down the filtration rate in comparison with that in the initial stage.

In the above case, on the upstream side of each of the first bypass pipe 81 and the second bypass pipe 82 in the flow direction of the liquid 12, when the liquid 12 is going to flow from the tubular member 3 having the relatively large inner diameter to the first bypass pipe 81 or the second bypass pipe 82 having the relatively small inner diameter, the flow of the liquid 12 is impeded. Hence the pressure of the liquid 12 is difficult to control by the circulation pump 4. In consideration of the above point, as illustrated in FIG. 11, the filtration filter 5 is preferably disposed downstream of both the first bypass pipe 81 and the second bypass pipe 82 in the flow direction of the liquid 12. With that arrangement, the liquid can be more stably filtered (concentrated) with the filtration filter 5.

The advantageous effects of the above embodiments can be obtained by combining optional ones among the above embodiments with each other as appropriate.

EXAMPLE

A practical example of obtaining the concentrate with filtration of the liquid 12 containing the filtration object 11 by using the concentration apparatus 1A according to Embodiment 2, as illustrated in FIG. 8, will be described below.

Here, the inner diameters of the tubular member 3 and the first bypass pipe 81 were each set to 4.3 mm. The inner diameter of the second bypass pipe 82 was set to 1.6 mm. The length of the tubular member 3 was set to 207 cm. The length of the circulation flow path shortened by the shunting with the first bypass pipe 81 was set to 172 cm. The length of the circulation flow path shortened by the shunting with the second bypass pipe 82 was set to 149 cm. Thus, the inner volume of the circulation flow path corresponding to the length of the tubular member 3 was about 30 ml. The inner volume of the circulation flow path shunt by the first bypass pipe 81 was about 25 ml. The inner volume of the circulation flow path shunt by the second bypass pipe 82 was 3 ml.

First, 500 ml of a cell suspension containing $5 \times 10^6$ cells was stored, as the liquid 12 containing the filtration object 11, in the liquid tank 2.

Then, the circulation pump 4 and the filtrate pump 6P were driven to circulate the cell suspension in the circulation flow path (see FIG. 5) corresponding to the length of the tubular member 3. At this time, a delivery rate of the circulation pump 4 was set to 200 ml/min, and a delivery rate of the filtrate pump 6P was set to 20 ml/min.

Then, when an amount of the cell suspension in the liquid tank 2 was reduced from 500 ml to 100 ml, the first valve 91 and the second valve 92 were switched to cause the cell suspension to circulate in the circulation flow path (see FIG. 6) shunt by the first bypass pipe 81. At this time, the delivery rate of the circulation pump 4 was set to 200 ml/min, and the delivery rate of the filtrate pump 6P was set to 10 ml/min. A time taken from the start of the filtration to the switching of the first valve 91 and the second valve 92 was about 20 min.

Then, when the amount of the cell suspension in the liquid tank 2 was reduced from 100 ml to 50 ml, the third valve 93 and the fourth valve 94 were switched to cause the cell suspension to circulate in the circulation flow path (see FIG. 7) shunt by the second bypass pipe 82. At this time, the delivery rate of the circulation pump 4 was set to 200 ml/min, and the delivery rate of the filtrate pump 6P was set to 10 ml/min. A time taken from the switching of the first valve 91 and the second valve 92 to the switching of the third valve 93 and the fourth valve 94 was about 5 min.

Then, when the amount of the cell suspension in the liquid tank 2 was reduced from 50 ml to 10 ml, the driving of the circulation pump 4 and the filtrate pump 6P were stopped. A time taken from the switching of the third valve 93 and the fourth valve 94 to the stop of the driving of the circulation pump 4 and the filtrate pump 6P was about 8 min. In other words, a time during which the cell suspension flowed through the second bypass pipe 82 was longer than a time during which the cell suspension flowed through the first bypass pipe 81.

Thus, in this EXAMPLE, a time taken to concentrate the cell suspension containing $5 \times 10^6$ cells from 500 ml to 10 ml was 33 min (=20 min+5 min+8 min). By the way, when the cell suspension was circulated in the circulation flow path (see FIG. 7) shunt by the second bypass pipe 82 from the start of the filtration, the time taken to concentrate the cell suspension containing $5 \times 10^6$ cells from 500 ml to 10 ml was 100 min or longer.

While the present invention has been fully described regarding preferred embodiments with reference to the accompanying drawings, various modifications and alterations of the preferred embodiments are apparent to those skilled in the art. It is to be understood that those modifications and alterations also fall within the scope of the present invention insofar as not departing from the scope defined in attached Claims.

Since a concentrate having a higher concentration can be obtained in a shorter time, the present invention is particularly useful in application to a concentration apparatus that obtains the concentrate by filtering a liquid containing a biological substance such as a cell.

REFERENCE SIGNS LIST 1, 1A, 1B, 1C, 1D concentration apparatus
2 liquid tank
3 tubular member
3a through hole
3A one end portion
3B other end portion
4 circulation pump
5 filtration filter
5A bypass-pipe filtration filter
6 filtrate discharge pipe
6A one end portion
6B other end portion
7 filtrate tank
11 filtration object
12 liquid
13 filtrate
51 metallic porous membrane
51a first principal surface
51b second principal surface
51c through-hole
52 frame member
52a first frame member
52b second frame member
81 first bypass pipe
81A one end portion
81B other end portion
82 second bypass pipe
82A one end portion
82B other end portion
91 first valve
92 second valve
93 third valve
94 fourth valve
CT control unit

The invention claimed is:
1. A concentration apparatus comprising:
a liquid tank storing a liquid containing a filtration object;
a tubular member having a first end portion and a second end portion, each of which being disposed in the liquid tank and forming a first circulation flow path between the first end portion and the second end portion;

a circulation pump for supplying the liquid stored in the liquid tank to flow from the first end portion to the second end portion of the tubular member in a circulating manner;
a filtration filter between the first end portion and the second end portion, the filtration filter including a metallic porous membrane sized to separate the filtration object from the liquid;
a bypass pipe having first and second ends thereof connected to sidewalls of the tubular member so as to form a second circulation flow path between the first end portion and the second end portion of the tubular member, the second circulation flow path having a shorter path length than the first circulation flow path, wherein the filtration filter is in the second circulation flow path formed by the bypass pipe;
a switching valve constructed to cause the liquid to flow in one of the first circulation flow path or the second circulation flow path; and
a control unit controlling driving of the circulation pump and a switching operation of the switching valve,
wherein, when an amount of the liquid in the liquid tank is at a threshold or below, the control unit is operable to switch the switching valve to cause the liquid to flow through the second circulation flow path.

2. The concentration apparatus according to claim 1, wherein, when a pressure or a flow speed of the liquid flowing in the first circulation flow path is at a threshold or below, the control unit is operable to switch the switching valve to cause the liquid to flow through the second circulation flow path.

3. The concentration apparatus according to claim 1, further comprising:
a filtrate pump constructed to promote part of the liquid flowing between the first end portion and the second end portion of the tubular member to pass through the filtration filter,
wherein the control unit is operable to reduce a driving force of the filtrate pump when the switching valve is switched to cause the liquid flowing in the first circulation flow path to flow through the second circulation flow path.

4. A concentration comprising:
a liquid tank storing a liquid containing a filtration object
a tubular member having a first end portion and a second end portion, each of which being disposed in the liquid tank and forming a first circulation flow path between the first end portion and the second end portion;
a circulation pump for supplying the liquid stored in the liquid tank to flow from the first end portion to the second end portion of the tubular member in a circulating manner;
a filtration filter between the first end portion and the second end portion, the filtration filter including a metallic porous membrane sized to separate the filtration object from the liquid;
a bypass pipe having first and second ends thereof connected to sidewalls of the tubular member so as to form a second circulation flow path between the first end portion and the second end portion of the tubular member, the second circulation flow path having a shorter path length than the first circulation flow path;
a switching valve constructed to cause the liquid to flow in one of the first circulation flow path or the second circulation flow path;
a control unit controlling driving of the circulation pump and a switching operation of the switching valve,
wherein, when an amount of the liquid in the liquid tank is at a threshold or below, the control unit is operable to switch the switching valve to cause the liquid to flow through the second circulation flow path; and
a filtrate pump constructed to promote part of the liquid flowing between the first end portion and the second end portion of the tubular member to pass through the filtration filter,
wherein the control unit is operable to reduce a driving force of the filtrate pump when the switching valve is switched to cause the liquid flowing in the first circulation flow path to flow through the second circulation flow path,
wherein the bypass pipe is a first bypass pipe, the driving force is a first driving force, and the concentration apparatus further comprises:
a second bypass pipe having first and second ends thereof connected to sidewalls of the tubular member so as to form a third circulation flow path between the first end portion and the second end portion of the tubular member, the third circulation flow path having a shorter path length than the second circulation flow path,
the switching valve is constructed to cause the liquid to flow in one of the first circulation flow path, the second circulation flow path, or the third circulation flow path, and
the control unit is operable to drive the filtrate pump with a second driving force smaller than the first drive force when the switching valve is switched to cause the liquid to flow through the third circulation flow path.

5. A concentration comprising:
a liquid tank storing a liquid containing a filtration object;
a tubular member having a first end portion and a second end portion, each of which being disposed in the liquid tank and forming a first circulation flow path between the first end portion and the second end portion;
a circulation pump for supplying the liquid stored in the liquid tank to flow from the first end portion to the second end portion of the tubular member in a circulating manner;
a filtration filter between the first end portion and the second end portion, the filtration filter including a metallic porous membrane sized to separate the filtration object from the liquid;
a bypass pipe having first and second ends thereof connected to sidewalls of the tubular member so as to form a second circulation flow path between the first end portion and the second end portion of the tubular member, the second circulation flow path having a shorter path length than the first circulation flow path;
a switching valve constructed to cause the liquid to flow in one of the first circulation flow path or the second circulation flow path:
a control unit controlling driving of the circulation pump and a switching operation of the switching valve,
wherein, when an amount of the liquid in the liquid tank is at a threshold or below, the control unit is operable to switch the switching valve to cause the liquid to flow through the second circulation flow path; and
a filtrate pump constructed to promote part of the liquid flowing between the first end portion and the second end portion of the tubular member to pass through the filtration filter,
wherein the control unit is operable to reduce a driving force of the filtrate pump when the switching valve is switched to cause the liquid flowing in the first circulation flow path to flow through the second circulation flow path, wherein the bypass pipe is a first bypass pipe, and the concentration apparatus further comprises:

a second bypass pipe having first and second ends thereof connected to sidewalls of the tubular member so as to form a third circulation flow path between the first end portion and the second end portion of the tubular member, the third circulation flow path having a shorter path length than the second circulation flow path, the switching valve is constructed to cause the liquid to flow in one of the first circulation flow path, the second circulation flow path, or the third circulation flow path, and the control unit is operable to switch the switching valve to make a time during which the liquid flows through the third circulation flow path longer than a time during which the liquid flows through the second circulation flow path.

6. The concentration apparatus according to claim 4, wherein the filtration filter is in a sidewall of the tubular member, and the concentration apparatus further comprises:

a first bypass-pipe filtration filter in a sidewall of the first bypass pipe, the first bypass-pipe filtration filter including a metallic porous membrane sized to separate the filtration object from the liquid; and a second bypass-pipe filtration filter in a sidewall of the second bypass pipe, the second bypass-pipe filtration filter including a metallic porous membrane sized to separate the filtration object from the liquid.

7. The concentration apparatus according to claim 5, wherein the filtration filter is in a sidewall of the tubular member, and the concentration apparatus further comprises:

a first bypass-pipe filtration filter in a sidewall of the first bypass pipe, the first bypass-pipe filtration filter including a metallic porous membrane sized to separate the filtration object from the liquid; and a second bypass-pipe filtration filter in a sidewall of the second bypass pipe, the second bypass-pipe filtration filter including a metallic porous membrane sized to separate the filtration object from the liquid.

8. A concentration comprising:

a liquid tank storing a liquid containing a filtration object a tubular member having a first end portion and a second end portion, each of which being disposed in the liquid tank and forming a first circulation flow path between the first end portion and the second end portion;

a circulation pump for supplying the liquid stored in the liquid tank to flow from the first end portion to the second end portion of the tubular member in a circulating manner;

a filtration filter between the first end portion and the second end portion, the filtration filter including a metallic porous membrane sized to separate the filtration object from the liquid;

a bypass pipe having first and second ends thereof connected to sidewalls of the tubular member so as to form a second circulation flow path between the first end portion and the second end portion of the tubular member, the second circulation flow path having a shorter path length than the first circulation flow path;

a switching valve constructed to cause the liquid to flow in one of the first circulation flow path or the second circulation flow path; and a control unit controlling driving of the circulation pump and a switching operation of the switching valve, wherein, when an amount of the liquid in the liquid tank is at a threshold or below, the control unit is operable to switch the switching valve to cause the liquid to flow through the second circulation flow path, wherein the bypass pipe is a first bypass pipe, and the concentration apparatus further comprises:

a second bypass pipe having first and second ends thereof connected to sidewalls of the tubular member so as to form a third circulation flow path between the first end portion and the second end portion of the tubular member, the third circulation flow path having a shorter path length than the second circulation flow path, the switching valve is constructed to cause the liquid to flow in one of the first circulation flow path, the second circulation flow path, or the third circulation flow path.

9. The concentration apparatus according to claim 8, wherein the filtration filter is in a sidewall of the tubular member, and the concentration apparatus further comprises:

a first bypass-pipe filtration filter in a sidewall of the first bypass pipe, the first bypass-pipe filtration filter including a metallic porous membrane sized to separate the filtration object from the liquid; and a second bypass-pipe filtration filter in a sidewall of the second bypass pipe, the second bypass-pipe filtration filter including a metallic porous membrane sized to separate the filtration object from the liquid.

10. The concentration apparatus according to claim 1, wherein the filtration filter is in a sidewall of the tubular member.

11. The concentration apparatus according to claim 1, wherein the bypass pipe has a smaller inner diameter than the tubular member.

12. The concentration apparatus according to claim 11, wherein the filtration filter is located downstream of the bypass pipe in a flow direction of the liquid toward the second end portion.

13. The concentration apparatus according to claim 4, wherein the first bypass pipe has a smaller inner diameter than the tubular member, and the second bypass pipe has a smaller diameter than the first bypass pipe.

14. The concentration apparatus according to claim 5, wherein the first bypass pipe has a smaller inner diameter than the tubular member, and the second bypass pipe has a smaller diameter than the first bypass pipe.

15. The concentration apparatus according to claim 8, wherein the first bypass pipe has a smaller inner diameter than the tubular member, and the second bypass pipe has a smaller diameter than the first bypass pipe.

* * * * *